(12) United States Patent
Lenormand et al.

(10) Patent No.: US 6,453,727 B1
(45) Date of Patent: Sep. 24, 2002

(54) METHOD OF EVALUATING PHYSICAL PARAMETERS OF AN UNDERGROUND RESERVOIR FROM ROCK CUTTINGS TAKEN THEREFROM

(75) Inventors: Roland Lenormand; Patrick Egermann, both of Rueil-Malmaison (FR)

(73) Assignee: Institut Francais Du Petrole, Rueil-Malmasion cedex (FR)

( * ) Notice: Subject to any disclaimer, the term of this patent is extended or adjusted under 35 U.S.C. 154(b) by 0 days.

(21) Appl. No.: 09/883,387

(22) Filed: Jun. 19, 2001

(30) Foreign Application Priority Data

Jun. 23, 2000 (FR) .............................................. 00 08059

(51) Int. Cl.⁷ .......................... G01N 15/08; G01N 5/02; E21B 49/00; G01V 3/02
(52) U.S. Cl. ...................... 73/38; 73/152.06; 73/152.05; 73/152.52; 166/250.02; 175/46
(58) Field of Search ................................ 73/38, 152.09, 73/152.06, 152.07, 152.05, 152.41, 152.52; 166/250.02, 252.5; 175/46, 50

(56) References Cited

U.S. PATENT DOCUMENTS

| | | | | |
|---|---|---|---|---|
| 4,381,665 A | * | 5/1983 | Levine et al. | 73/73 |
| 4,420,975 A | * | 12/1983 | Nagel et al. | 73/155 |
| 5,050,493 A | * | 9/1991 | Prizio et al. | 100/106 |
| 5,069,065 A | * | 12/1991 | Sprunt et al. | 73/153 |
| 5,164,672 A | * | 11/1992 | Gilliland et al. | 324/376 |

(List continued on next page.)

FOREIGN PATENT DOCUMENTS

FR 2772483 12/1997 .......... G01N/33/00

OTHER PUBLICATIONS

A.F. Marsala, et al.: "Transient method inplemented under unsteady–state conditions for low and very low permeabitity measurements on cuttings", SPE/IRSM EUROCK '98, Jul. 8, 1998, pp. 33–39, XP000992311 Trondheim.

Lenormad, et al.: "Can we really measure the relative permeabilities using the micropore membrane method?", Journal of Petroleum Science and Engineering, vol. 19, No. 1–2, Jan. 1998, pp. 93–102, XP000991162, issn 0920–4105 Elsevier Science Amsterdam.

French Search Report w/partial translation.

*Primary Examiner*—Hezron Williams
*Assistant Examiner*—David J. Wiggins
(74) *Attorney, Agent, or Firm*—Antonelli, Terry, Stout & Kraus, LLP

(57) ABSTRACT

System of evaluating physical parameters such as the absolute permeability of porous rocks of a zone of an underground reservoir, from fragments taken from this zone, such as rock cuttings carried along by the drilling mud.

Rock fragments (F) are immersed in a viscous fluid contained in a vessel (1). Pumping means (2, 3) first inject into vessel (1) a fluid under a pressure that increases with time, up to a determined pressure threshold, so as to compress the gas trapped in the pores of the rock. This injection stage is followed by a relaxation stage with injection stop. The pressure variation measured by detectors (7, 8) during these two successive stages is recorded by a computer (9). The evolution of the pressure during the injection process being modelled from initial values selected for the physical parameters of the fragments, the computer adjusts them iteratively so as to best get the modelled pressure curve to coincide with the pressure curve really measured.

Application: petrophysical measurement.

5 Claims, 4 Drawing Sheets

U.S. PATENT DOCUMENTS

| | | | |
|---|---|---|---|
| 5,167,139 A | * 12/1992 | Lafargue et al. | 73/38 |
| 5,261,267 A | * 11/1993 | Kamath et al. | 73/38 |
| 5,269,180 A | * 12/1993 | Dave et al. | 73/152 |
| 5,297,420 A | * 3/1994 | Gilliland et al. | 73/38 |
| 5,394,737 A | * 3/1995 | Prange et al. | 73/38 |
| 5,513,515 A | * 5/1996 | Mayer | 73/38 |
| 5,520,248 A | * 5/1996 | Sisson et al. | 166/250.02 |
| 5,637,796 A | * 6/1997 | Deruyter et al. | 73/152.09 |
| 5,679,885 A | * 10/1997 | Lenormand et al. | 73/38 |
| 5,832,409 A | * 11/1998 | Ramakrishnan et al. | 702/12 |
| 5,844,136 A | * 12/1998 | Marsala et al. | 73/38 |
| 6,098,448 A | * 8/2000 | Lowry et al. | 73/38 |
| 6,241,019 B1 | * 6/2001 | Davidson et al. | 166/249 |

* cited by examiner

METHOD OF EVALUATING PHYSICAL PARAMETERS OF AN UNDERGROUND RESERVOIR FROM ROCK CUTTINGS TAKEN THEREFROM

FIELD OF THE INVENTION

The present invention relates to a method and to a device for evaluating the absolute permeability of a zone of an underground hydrocarbon reservoir from rock samples taken from this zone, such as cuttings obtained during well drilling operations.

The current petroleum context leads operators to taking an interest in new zones (deep offshore) and in new types of reservoirs (marginal structures close to existing surface installations). Considering the drilling costs linked with the difficult environment of these new discoveries or with the limited size of certain structures, operators can no longer allow themselves to drill complementary appraisal wells without taking the risk of compromising the economic viability of the project. The development strategy set before starting production is therefore less strict so as to allow <<real time>> adaptation to the nature of the information collected as a result of production well drilling, which is referred to as appraisal development.

Petrophysical measurements play a key part in the appraisal of the quality of a reservoir. However, the delays linked with this type of measurement are often very long and thus incompatible with the reactivity required for the success of such appraisal developments. New, faster and less expensive evaluation means are therefore sought as a decision-making support.

The cuttings carried along by the mud have been subjected to in-situ examinations for a long time. They are carried out by the teams in charge of mud logging operations and they are essentially intended to complete the description of the geologic layers crossed through during drilling, which is performed from logs.

BACKGROUND OF THE INVENTION

Work has already been done to evaluate petrophysical properties from cuttings. Acoustic properties relative to S and P waves have been measured for example. Various parameters have also been studied, such as the hardness and the deformation of rock fragments, or the porosity and the permeability thereof.

According to a first known permeability measurement method, the rock fragment is previously coated with resin. A thin slice is cut from the coated rock and placed in a measuring cell. It comprises means for injecting a fluid under pressure at a controlled flow rate and means for measuring the pressure drop created by the sample. Since the resin is impermeable, the absolute permeability is deduced from Darcy's equation by taking into account the real surface area occupied by the cuttings.

This method is for example described by:

Santarelli F. J. et al; <<Formation evaluation from logging on cuttings>>, SPERE, June 1998, or Marsala A. F. et al; <<Transient Method Implemented under Unsteady State Conditions for Low and Very Low Permeability Measurements on Cuttings>>; SPE/ISRM No.47202, Trondheim, Jul. 8–10, 1998.

This type of measurement can only be obtained in the laboratory after long cuttings conditioning operations.

Another method is based on an NMR (Nuclear Magnetic Resonance) measurement that is performed directly on the cuttings after previous washing followed by brine saturation. This type of measurement gives a directly exploitable porosity value. Permeability K is determined by means of correlations of the same nature as those used within the scope of NMR logging.

An illustration of this method can be found in the following document:

Nigh E. et al; P–K™: <<Wellsite Determination of Porosity and Permeability Using Drilling Cuttings>>, CWLS Journal, Vol.13, No.1, December 1984.

SUMMARY OF THE INVENTION

The object of the method according to the invention is to evaluate physical parameters such as the absolute permeability of porous rocks of an underground reservoir zone from rock fragments (cuttings for example) taken from this zone.

The method comprises:

immersing the fragments in a viscous fluid contained in a containment vessel, a stage of injection, into the vessel, of the viscous fluid under a pressure that increases with time, up to a determined pressure threshold, so as to compress the gas trapped in the pores of the rock, a relaxation stage after injection stop, measuring the evolution of the pressure in the vessel during the two injection and relaxation stages, modelling the evolution of the pressure during the injection and relaxation process, from initial values selected for the physical parameters of the fragments, and a stage of iterative adjustment of the physical parameter values of the rock fragments so that the modelled evolution is best adjusted to the measured pressure evolution in the vessel.

According to the circumstances, the containment vessel can be filled with cuttings invaded by drilling fluids or previously cleaned.

The device according to the invention allows to evaluate physical parameters such as the absolute permeability of porous rocks of an underground reservoir zone, from rock fragments taken from this zone. It essentially comprises:

a containment vessel for porous rock fragments, means for injecting a viscous fluid into the vessel in order first to fill the vessel containing the rock fragments, and to perform a cycle comprising a stage of injection, into the vessel, of fluid under a pressure that increases with time (preferably at a constant flow rate to facilitate measurement of the volume of fluid injected), up to a determined pressure threshold, then to compress the gas trapped in the pores of the rock, and a relaxation stage after injection stop, means for measuring the evolution of the pressure in the vessel during the two injection and relaxation stages, and a processing system for modelling the evolution of the pressure during the injection and relaxation process, from initial values selected for the physical parameters of the rock fragments, and for iteratively adjusting the values to be given to these physical parameters so that the modelled pressure evolution is best adjusted to the measured pressure evolution in the vessel.

The injection means comprise for example a pump injecting water at a constant flow rate into a surge tank filled with a high-viscosity oil communicating with the containment vessel through valves.

The method is satisfactory for rocks of very different permeabilities ranging from some millidarcy to several hundred millidarcy. Considering the limited surface area occupied by the implementation device and the speed with which the measurements and the adjustment between the theoretical data and the experimental data can be performed, the method lends itself particularly well to field conditions. It is thus quite possible to envisage measurement and interpretation directly on the site within a very short time, therefore with no possible comparison with those required to obtain equivalent results by means of laboratory methods. This opens up interesting possibilities as regards characterization since this new source of information can be put to good use as a support for interpretation of electric logs and to fine down evaluation of a well in terms of production potential.

BRIEF DESCRIPTION OF THE DRAWINGS

Other features and advantages of the method and of the device according to the invention will be clear from reading the description hereafter of non limitative examples, with reference to the accompanying drawings wherein.

DETAILED DESCRIPTION

As mentioned above, determination of physical parameters of rocks such as the absolute permeability thereof, for example, essentially comprises three stages:

I) a stage of acquisition of experimental measurements of the pressure variations from cuttings, leading to experimental curves, II) a stage of modelling the physical phenomena that appear in the cuttings during this operating cycle, for arbitrary values of the physical parameters sought (permeability K) involved in the model, allowing to establish similar theoretical curves, and III) an adjustment stage where the values to be given to the physical parameters involved in the model are determined so as to obtain best adjustment of the experimental curves and of the theoretical curves.

I) Measurement acquisition

Figure 1:
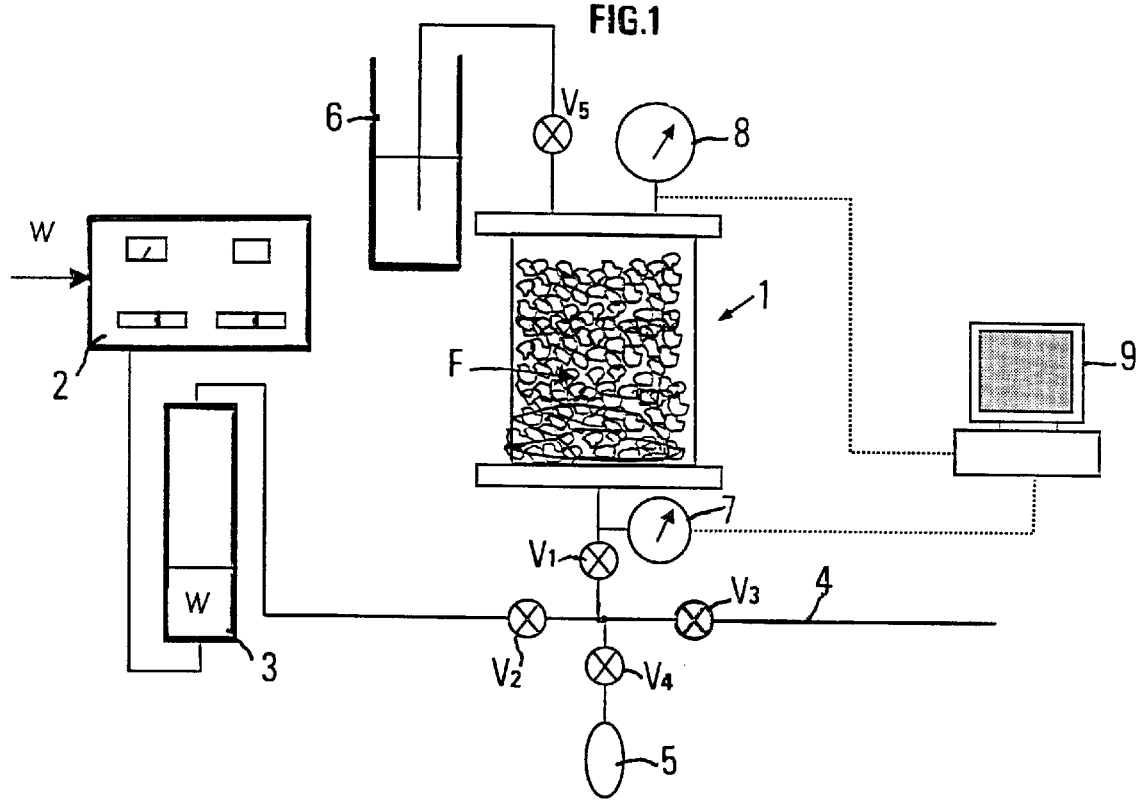
FIG. 1 diagrammatically shows the device.

The first stage is carried out by means of a device as diagrammatically shown in FIG. 1. It comprises a containment vessel 1 in which the cuttings F are initially introduced. A constant delivery rate water pump 2 communicates through a line 3 with the base of a surge tank 4 containing a high-viscosity oil. The opposite end of surge tank 4 communicates with a first end of containment vessel 1. A series of valves V1 to V4 allows selective communication of vessel 1 with surge drum 3 containing the oil and with a drain line 4, and isolation thereof. The opposite end of containment vessel 1 communicates via an isolating valve V5 with a separator 6. Two manometers 7, 8 are respectively connected to the opposite ends of vessel 1. The pressure variations measured by manometers 7, 8 are acquired by a computer 9.

The vessel is first filled with cuttings. The latter can be cuttings that are immediately available on the site, i.e. invaded by drilling mud and gas released by decompression.

It is also possible to use cuttings available after cleaning, from which all the fluids have been previously drawn away. In cases where containment vessel 1 is filled with cleaned cuttings, helium coming from a bottle 5 is injected so as to expel the air contained in the vessel.

Vessel 1 is then filled with a high-viscosity oil. The oil occupies the free space between the cuttings and it also enters the rock by spontaneous imbibition. A degassing process occurs, whose intensity and duration depends on the nature of the rock (mainly the porosity thereof). This degassing process only affects part of the gas. A certain residual volume remains trapped in the cuttings in form of disconnected clusters.

An oil injection is then performed (at a constant injection rate, for example, so as to readily measure the amount of oil that has entered the pores of the rock) with a gradual pressure rise stage (part C1 of the pressure curve) as the residual gas trapped in the pores is compressed. When the pressure reaches a determined threshold $P_M$, oil injection is stopped. A stabilization occurs then. The fluids tend to rebalance in the cuttings and a slow return to pressure equilibrium (part C2 of the pressure curve) is observed.

FIGS. 3a to 3d show examples of evolution of the pressure signal observed for cuttings of four different rocks with a flow rate of 480 cc/h. Whatever the rock considered, the same general pressure evolution is observed. A progressive increase is noticed during the injection stage as the residual gas is compressed. The time required to increase the pressure by 5 bars ranges, according to rocks, from 15 to 40 seconds depending on the initial volume of trapped gas. As soon as injection is stopped, the pressure decreases. Although this decrease is significant for rocks 1 and 2, it remains more moderate for rocks 3 and 4. A gradual stabilization of the signal can be observed in the long run.

II) Modelling

The object of this modelling process is to obtain an estimation of permeability K from the pressure measurements.

The cuttings are considered to be of homogeneous size and of spherical shape, and the gas is assumed to be perfect. The pressure drop linked with the viscosity of the gas is disregarded in relation to that of the oil, considering the difference between the viscosities thereof. The residual gas trapped in the cuttings after spontaneous imbibition of the oil takes the form of disconnected clusters that are homogeneously distributed. The capillary pressure is also considered to be negligible.

Figure 2:
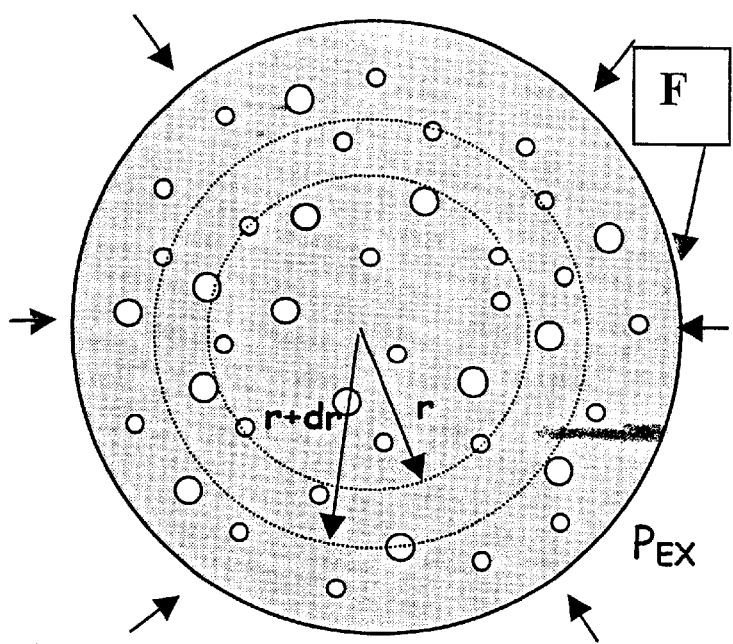
FIG. 2 diagrammatically shows the structure of a porous rock cutting or particle wherein the effects of the injection of a high-viscosity fluid such as oil are modelled, FIGS. 3a to 3c diagrammatically show the variation curves of the pressure prevailing in the vessel of the device of FIG. 1, during the injection and relaxation stages, for four different rocks.
Figure 3A:
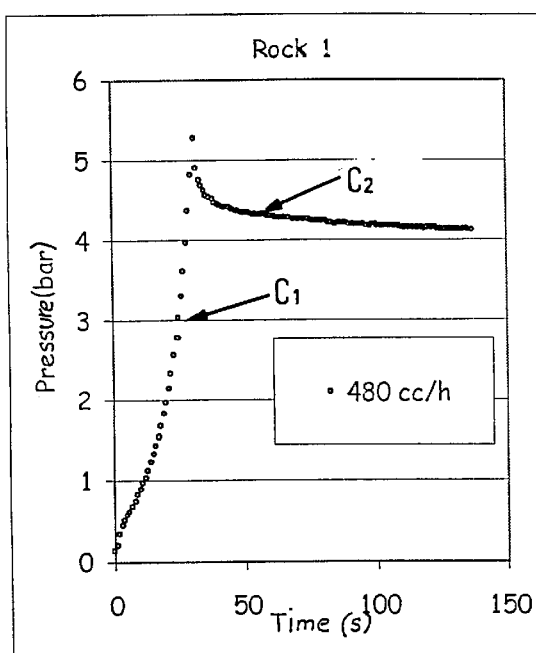
Figure 3B:
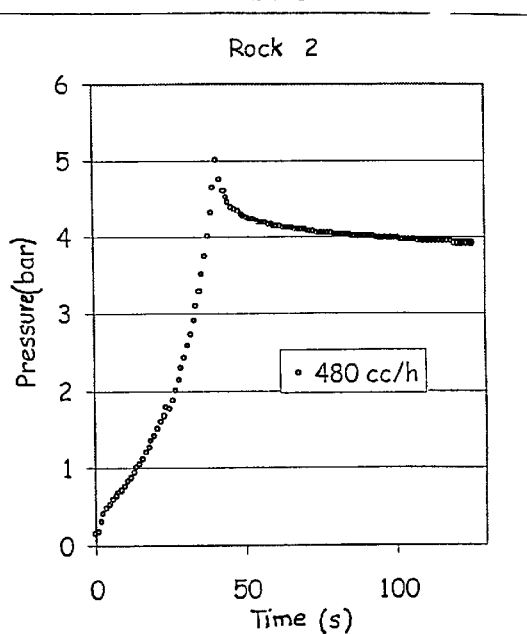
Figure 3C:
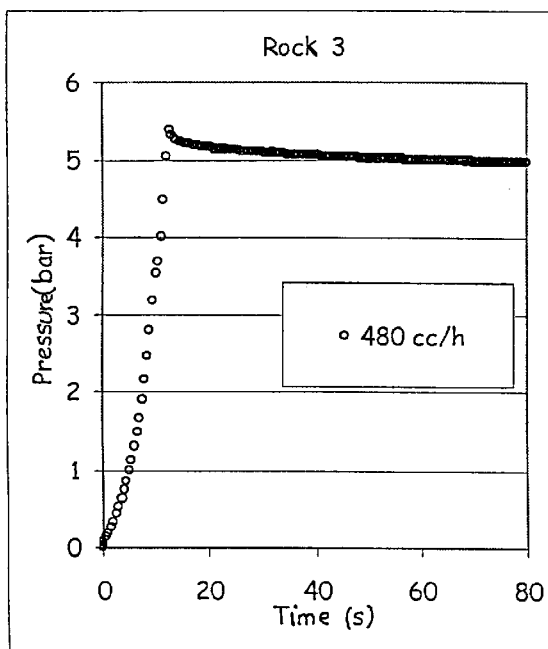
Figure 3D:
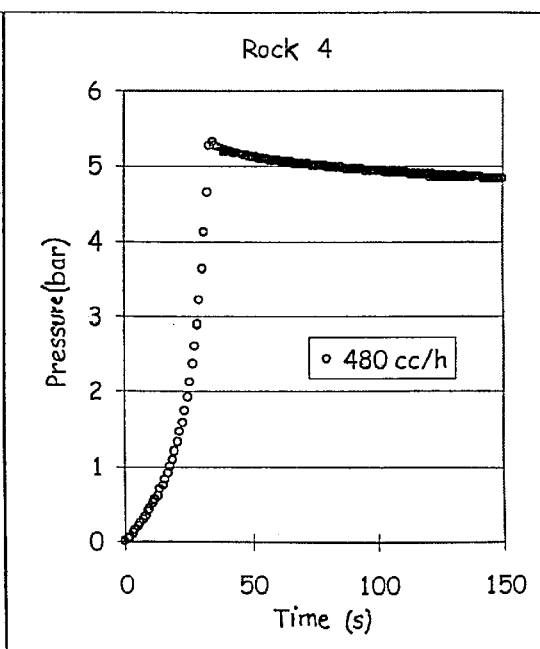

Considering the spherical shape of the cuttings, one will reason on the basis of a cap of thickness dr (FIG. 2) and calculate the evolution of the pressure at the boundary of the rock particle when a flow of oil q is injected.

One considers that the total flow rate Q of the injected fluid is equitably divided among the N rock particles, and that each one receives flow rate $$q = \frac{Q}{N}.$$

The gas law allows to deduce the local gas saturation Sg from the moment that pressure P:

$$S_g = S_{g0} \frac{P_0}{P}$$

is known ($P_0$ is the pressure of the oil). A material balance is made on the oil in the cap. The accumulation is equal to the difference between the inflow and the outflow. We thus deduce therefrom:

$$div\vec{V_0} + \phi \frac{\partial S_0}{\partial t} = 0.$$

Since $S_0 = (1-S_g) = (1-S_{g0} P_0/P)$, we deduce therefrom that:

$$\frac{\partial S_0}{\partial t} = \frac{\partial S_0}{\partial P}\frac{\partial P}{\partial t} = \left(S_{g0}\frac{P_0}{P^2}\right)\frac{\partial P}{\partial t}.$$

Besides, since $$\vec{V_0} = -\frac{K}{\mu_0}$$

$\vec{gr\,a}\,dP_0$ and the capillary pressure can be considered to be negligible, which gives $P_0 = P_{gas} = P$, the previous equation can be written as follows:

$$-\frac{K}{\mu_0}\Delta P + \phi S_{g0} \frac{P_0}{P^2}\frac{\partial P}{\partial t} = 0.$$

It follows therefrom that:

$$\Delta P = \frac{\mu_0 \phi S_{g0}}{K}\frac{P_0}{P^2}\frac{\partial P}{\partial t}.$$

We thus obtain the conventional form of a diffusion type equation with, however, a $1/P^2$ accumulation factor term that is due to the compressible nature of the gas.

In spherical coordinates, the Laplacian is equal to $$\frac{1}{r^2}\frac{\partial}{\partial r}\left(r^2 \frac{\partial P}{\partial r}\right).$$

Finally, the equation to be solved is written as follows:

$$\frac{\partial}{\partial r}\left(r^2 \frac{\partial P}{\partial r}\right) = \alpha \frac{r^2}{P^2}\frac{\partial P}{\partial t} \qquad (1)$$

with $$\alpha = \frac{\mu_0 \phi S_{g0} P_0}{K} \qquad (2)$$

As it is injected, the oil expels the air in the free space between the cuttings and it enters the rock by spontaneous imbibition. Despite certain precautions, a certain volume of gas may remain outside as a result of the non-regular shape of the cuttings. This trapped volume ($V_{gp}$) has a direct effect on the general form of the pressure response and it has to be taken into account in the solution.

A certain compressibility due to the experimental device also has to be taken into account. It results from the vessel, from the lines as well as from the properties of the oil. The equivalent compressibility observed is of the order of 0.0005 $bar^{-1}$.

Since the oil used is saturated with gas at atmospheric pressure, dissolution phenomena appear when the pressure increases during measurement. These aspects are taken into account by introducing a diffusion parameter expressing the molecule exchanges at the gas-oil interfaces.

The diffusion equation is solved by means of the finite difference method with an explicit pattern and by applying the boundary conditions in time $P(r,0) = P_{atm}$ and in space $P(R,t) = P_{ext}$ and $$\frac{\partial P}{\partial r}(0, t) = 0.$$

The convergence test on $P_{ext}$ is based on a comparison between the saturation in gas remaining in the rock particle and the value obtained by volume balance from the amount of oil injected.

Solution of the diffusion equation during the relaxation period is identical. Only the test condition changes since the injection stop leads to maintaining the volume of gas in the rock particle.

III) Adjustment of the model to the experimental results

The model is implemented in a calculator such as computer 9 (see FIG. 1) in form of a software and included in an iterative optimization loop. The model is <<run>> with a priori values selected for permeability K, factors $\Phi$ and $S_{g0}$ involved in relation 2 by their product, the resulting simulated pressure curve is compared with the experimental curve and, by successive iterations where the previous values are changed in the model, those allowing best adjustment of the theoretical curve and of the experimental curve are found.

Figure 4:
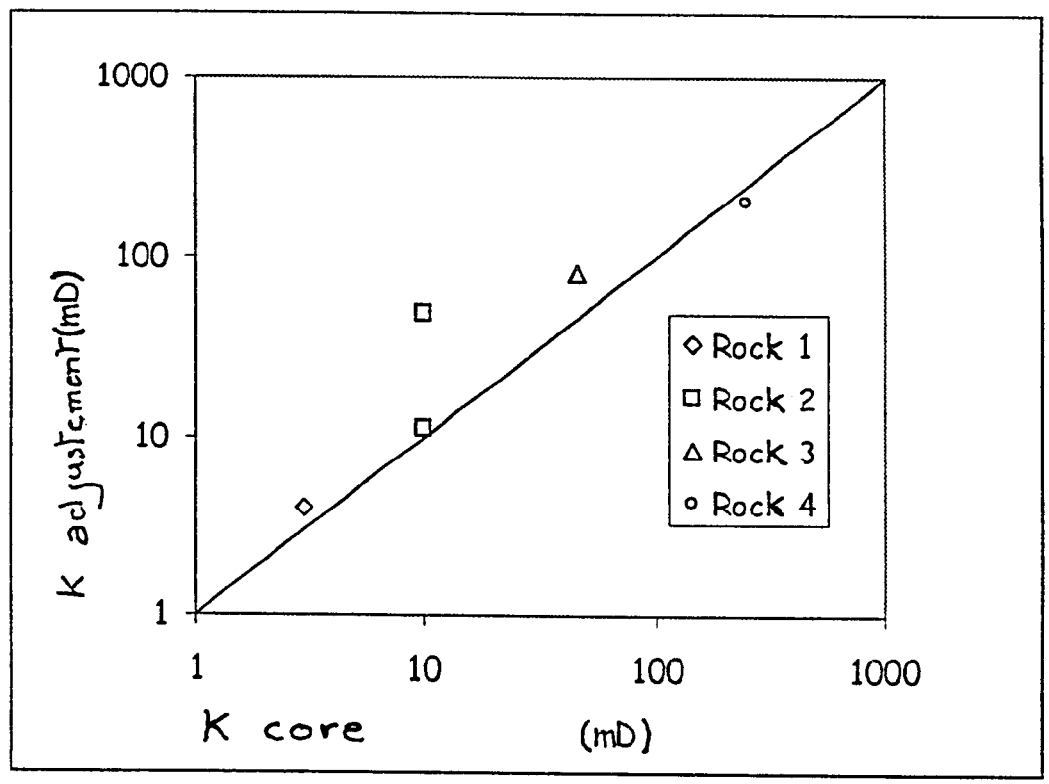
FIG. 4 shows the accordance between the permeabilities obtained for four rock particles, by means of a conventional core testing method and by the method according to the invention.
Figure 5A:
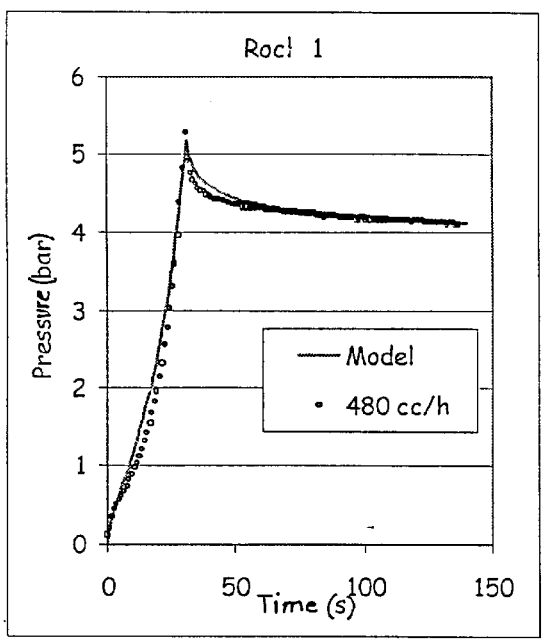
FIGS. 5a to 5d show, for the previous four rocks, the accuracy that can be obtained when adjusting the modelled pressure curves in relation to the experimental curves.
Figure 5B:
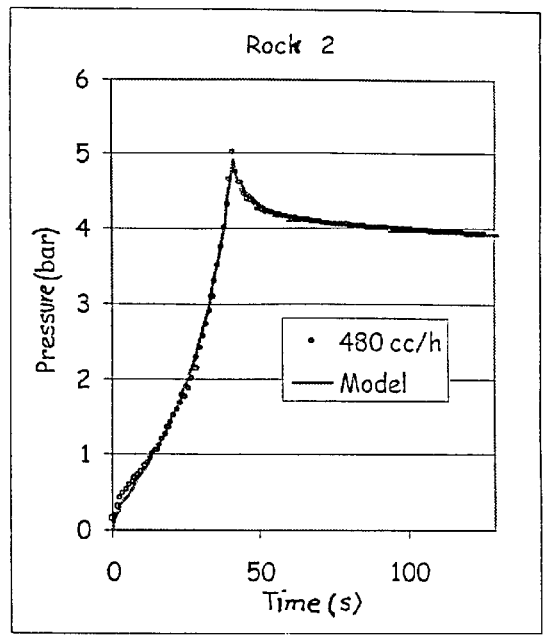
Figure 5C:
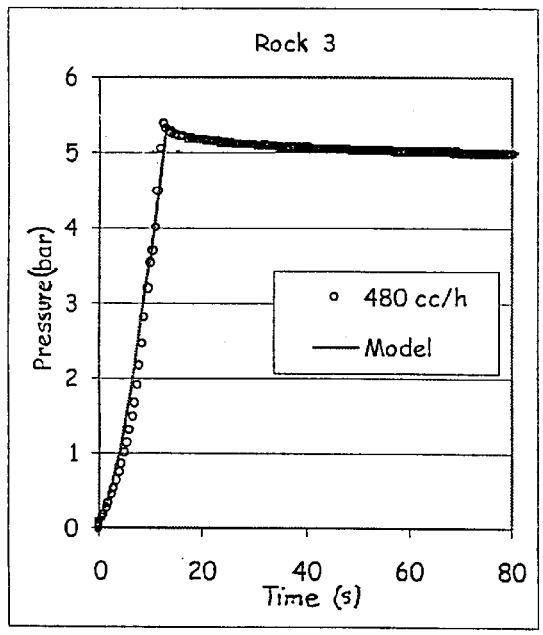
Figure 5D:
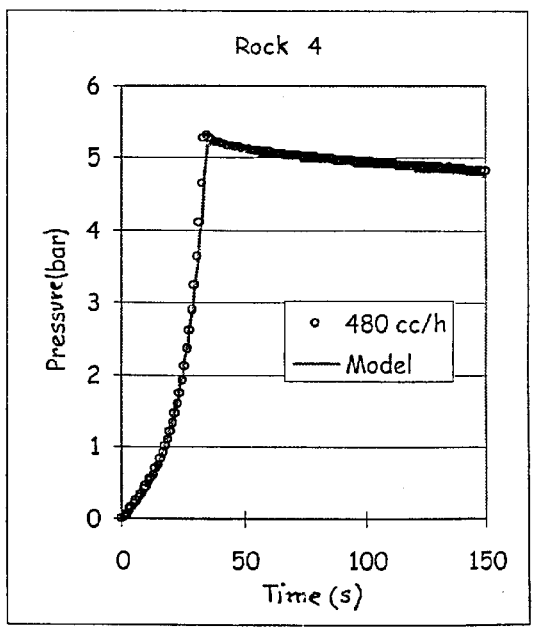

FIGS. 5a to 5d show the accordance that is rapidly obtained, by successive iterations, between the theoretical curve and the experimental curve for the previous four rock fragments. As can also be seen in FIG. 4, the results obtained by applying the method are quite comparable, for the four rocks, with those obtained in the laboratory after long conditioning times using conventional methods. This modelling process is programmed within a code, which allows to adjust the experiments by trial and error, and thus to deduce the corresponding value of K.

We claim:

1. A method of evaluating physical parameters such as the absolute permeability of porous rocks of a zone of an underground reservoir, from fragments taken from this zone, characterized in that it comprises:

immersing fragments (F) in a viscous fluid contained in a containment vessel (1), a stage of injection, into the vessel, of this fluid under a pressure that increases with time, up to a determined pressure threshold, so as to compress the gas trapped in the pores of the rock, a relaxation stage with injection stop, measuring the evolution of the pressure in vessel (1) during the two injection and relaxation stages, modelling the evolution of the pressure during the injection and relaxation process, from initial values selected for the physical parameters of fragments (F), and a stage of iterative adjustment of the values of the physical parameters of the rock fragments so that the modelled evolution is best adjusted to the measured evolution of the pressure in the vessel.

2. A method as claimed in claim 1, characterized in that the containment vessel is filled with cuttings invaded by drilling fluids.

3. A method as claimed in claim 1, characterized in that the containment vessel is filled with cuttings that have been previously cleaned.

4. A device for evaluating physical parameters such as the absolute permeability of porous rocks of a zone of an underground reservoir, from rock fragments taken from this zone, characterized in that it comprises:

a containment vessel (1) for porous rock fragments (F), means (2, 3) for injecting a viscous fluid into vessel (1) so as to first fill the vessel containing the rock fragments and then to perform a cycle comprising a stage of injection of the fluid into the vessel under a pressure that increases with time, up to a determined pressure threshold ($P_M$), so as to compress the gas trapped in the pores of the rock, and a relaxation stage with injection stop, means (7, 8) for measuring the evolution of the pressure in vessel (1) during the injection and relaxation stages, and a processing system (9) for modelling the evolution of the pressure during the injection and relaxation process, from initial values selected for the physical parameters of the rock fragments, and for iteratively adjusting the values to be given to these physical parameters so that the modelled pressure evolution is best adjusted to the measured pressure evolution in the vessel.

5. A device as claimed in claim 4, characterized in that the injection means comprise a pump (2) injecting water at a constant flow rate into a surge tank (3) filled with high-viscosity oil.

* * * * *